(12) United States Patent
Bulloch et al.

(10) Patent No.: US 8,529,579 B2
(45) Date of Patent: Sep. 10, 2013

(54) APPARATUS, SYSTEM, AND METHOD FOR INTRA-ORAL DISTRACTION

(75) Inventors: Scott E. Bulloch, St. George, UT (US); Russell G. Olsen, Cedar City, UT (US)

(73) Assignee: Intrinsic Medical, LLC, Cedar City, UT (US)

( * ) Notice: Subject to any disclaimer, the term of this patent is extended or adjusted under 35 U.S.C. 154(b) by 0 days.

(21) Appl. No.: 13/495,957

(22) Filed: Jun. 13, 2012

(65) Prior Publication Data

US 2012/0259332 A1   Oct. 11, 2012

Related U.S. Application Data

(62) Division of application No. 12/257,054, filed on Oct. 23, 2008, now abandoned.

(51) Int. Cl.
*A61B 17/60* (2006.01)

(52) U.S. Cl.
USPC ............................ 606/105; 606/57

(58) Field of Classification Search
USPC .................. 606/55, 57, 58, 90, 71, 105, 282, 606/320
See application file for complete search history.

(56) References Cited

U.S. PATENT DOCUMENTS

| | | | |
|---|---|---|---|
| 4,323,345 A | 4/1982 | Wallshein | |
| 4,541,422 A | 9/1985 | de Zbikowski | |
| 4,571,177 A | 2/1986 | Dahan | |
| 4,929,247 A | 5/1990 | Rayhack | |
| 5,147,358 A | 9/1992 | Remmler | |
| 5,364,396 A | 11/1994 | Robinson et al. | |
| 5,439,377 A | 8/1995 | Milanovich | |
| 5,540,687 A | 7/1996 | Fairley et al. | |
| 5,575,790 A | 11/1996 | Chen et al. | |
| 5,769,850 A | 6/1998 | Chin | |
| 5,855,580 A | 1/1999 | Kreidler et al. | |
| 5,885,290 A | 3/1999 | Guerrero et al. | |
| 5,895,387 A | 4/1999 | Guerrero et al. | |
| 5,902,304 A | 5/1999 | Walker et al. | |
| 6,086,365 A * | 7/2000 | Fields | ............................ 433/18 |
| 6,113,599 A | 9/2000 | Landsberger | |
| 6,277,124 B1 | 8/2001 | Haag | |
| 6,358,255 B1 | 3/2002 | Testa | |
| 6,423,069 B1 | 7/2002 | Sellers | |
| 6,471,706 B1 | 10/2002 | Schumacher et al. | |

(Continued)

OTHER PUBLICATIONS

U.S. Appl. No. 12/257,054 Office Action mailed Apr. 26, 2011.

(Continued)

*Primary Examiner* — Pedro Philogene
*Assistant Examiner* — Lynnsy Schneider
(74) *Attorney, Agent, or Firm* — Kunzler Law Group, PC (57) ABSTRACT

According to one representative embodiment, a method for distracting a segment of bone from a source bone includes providing a bone distractor that has a first end portion and a second end portion movable relative to each other. The method further includes coupling the first end portion to the segment of bone and coupling the second end portion to an anchor bone opposing the source bone. Additionally, the method includes actuating the bone distractor to move the first and second end portions closer to each other and pull the segment of bone toward the anchor bone. The method can also include fixing the source bone relative to the anchor bone. Further, the method can include positioning the bone distractor to the sides of the source bone, anchor bone, and a gingival layer covering the bones.

12 Claims, 5 Drawing Sheets

(56) References Cited

U.S. PATENT DOCUMENTS

| | | |
|---|---|---|
| 6,554,834 B1 | 4/2003 | Crozet et al. |
| 6,884,243 B2 | 4/2005 | Sellers |
| 6,908,469 B2 | 6/2005 | Sellers et al. |
| 7,182,785 B2 | 2/2007 | Elsalanty et al. |
| 7,252,668 B2 | 8/2007 | Wolgen |
| 7,337,883 B2 | 3/2008 | Geyer |
| 7,588,579 B2 | 9/2009 | Mommaerts |
| 2002/0116002 A1 | 8/2002 | Sellers |
| 2003/0050641 A1 | 3/2003 | Mommaerts |
| 2003/0144669 A1* | 7/2003 | Robinson ................ 606/90 |
| 2003/0233093 A1 | 12/2003 | Moles et al. |
| 2004/0152046 A1* | 8/2004 | Minoretti et al. ............ 433/173 |
| 2004/0199094 A1 | 10/2004 | Greene et al. |
| 2005/0043731 A1 | 2/2005 | Labbe et al. |
| 2005/0251136 A1 | 11/2005 | Noon et al. |
| 2007/0043370 A1 | 2/2007 | Ueda et al. |
| 2007/0276502 A1* | 11/2007 | Elsalanty et al. .......... 623/17.17 |
| 2008/0039861 A1 | 2/2008 | Ahmad et al. |
| 2008/0311542 A1 | 12/2008 | Rana et al. |
| 2009/0192514 A1 | 7/2009 | Feinberg et al. |
| 2009/0222006 A1 | 9/2009 | Allison |

OTHER PUBLICATIONS

U.S. Appl. No. 12/257,054 Office Action mailed Oct. 27, 2011.
U.S. Appl. No. 12/257,054 Final Office Action mailed Mar. 23, 2012.
PCT/US2009/061922, International Search Report and Written Opinion, May 25, 2010.

* cited by examiner

APPARATUS, SYSTEM, AND METHOD FOR INTRA-ORAL DISTRACTION

CROSS-REFERENCE TO RELATED APPLICATION

This application is a divisional application of U.S. patent application Ser. No. 12/257,054, filed Oct. 23, 2008, which is incorporated herein by reference.

FIELD

This invention relates to bone distraction and more particularly to intra-oral bone distraction.

BACKGROUND

Distraction osteogenesis is the process of lengthening bone tissue by cutting a bone segment from a source bone and gradually moving the bone segment away from the bone. The ends of the bone segment and source bone along the cut line are spaced apart to allow the formation of new bone tissue within the gap between the bone segment and source bone. As the bone segment is gradually moved away from the source bone, new bone tissue continues to grow between the bone segment and source bone until a desired length of the source bone, e.g., a desired increase in the length of the source bone, is reached. After the desired bone length is reached, the new bone tissue is allowed to heal until the tissue reaches an appropriate density the same as or similar to the source bone.

Traditionally, distraction osteogenesis techniques were limited to the field of orthopedics. Recently, however, distraction osteogenesis techniques have been applied to correct deformities of the jaw. Such jaw bone distraction techniques typically involve cutting away a bone segment from a source jaw bone, e.g., one of the maxilla or mandible jaw bones, securing a distraction device to the bone segment and the source jaw bone, and adjusting the distraction device to push the bone segment away from the source jaw bone.

Conventional jaw bone distraction techniques and devices suffer from several drawbacks. For example, pushing a bone segment away from the source jaw bone reduces the force vector control of the moving segment. Additionally, current bone distraction devices that push the bone segment away from the source jaw bone are typically attached or embedded within a patient's tissue, which can limit access and adjustment of the distractor and increase the risk of infection. Further, current bone distraction devices have a single threaded rod that facilitates adjusting of the devices. Such a configuration results in a distraction device with a limited action to length ratio, e.g., range of motion of the distraction device to overall minimum length ratio. In other words, the distance the distractor is able to push the bone segment is relatively small compared to the minimum overall length of the distractor itself. This results in a large device with a small range of motion.

SUMMARY

The subject matter of the present application has been developed in response to the present state of the art, and in particular, in response to the problems and needs in the art that have not yet been fully solved by currently available bone distraction apparatus, systems, and methods. Accordingly, the subject matter of the present application has been developed to provide a bone distractor and associated apparatus, systems, and methods that overcome at least some shortcomings of the prior art.

According to one embodiment, a bone distraction system for distracting a portion of bone from a source bone includes a first anchor portion couplable to an anchor bone and a second anchor portion couplable to a distractable bone segment of the source bone. The system includes a distractor coupling the first anchor portion and the second anchor portion. The overall length of the distractor is decreasable to pull the distractable bone segment toward the anchor bone for distracting the bone segment.

In certain implementations, the distractor includes a first end portion couplable to the first anchor portion, a second end portion couplable to the second anchor portion, and a telescoping portion extendable between the first and second end portions. The telescoping portion can be rotatable relative to the first and second end portions such that rotation of the telescoping portion reduces a distance between the first and second portions. In specific instances, the telescoping portion comprises a first threaded rod and a second threaded rod, the first and second threaded rods being rotatable relative to each other. The distractor can also include at least one support member adjacent the telescoping portion and extendable between the first and second end portions.

In some implementations, the ratio of a maximum range of linear motion of the distractor to a minimum overall length of the distractor is greater than about 11:15. In yet some implementations, the overall length of the distractor is adjustable between a maximum length and a minimum length. The ratio of the maximum length to the minimum length can be at least about 21:9.

The anchor bone can be one of the maxilla jaw bone and mandible jaw bone and the source bone can be the other of the maxilla jaw bone and mandible jaw bone. According to some implementations, when the first anchor portion is coupled to the anchor bone and the second anchor portion is coupled to the distractable bone segment, the distractor is external relative to the anchor bone, bone segment, and any tissue covering the anchor bone and bone segment.

In certain implementations, at least one of the first and second anchor portions of the system include a generally Y-shape having at least two spaced-apart eyelets each configured to receive a respective anchor. Further, the first and second anchor portions can each include at least one anchor that has a threaded portion and a head portion. The threaded portion can be embeddable within one of the anchor bone and bone segment and the head portion can include a plurality of flexible members According to yet another embodiment, a distractor for distracting a bone segment cut from a first jaw bone includes a first end portion couplable to one of the bone segment and a second jaw bone spaced apart from the first jaw bone. The distractor also includes a second end portion couplable to the other of the bone segment and the second jaw bone. Further, the distractor includes at least one telescoping member extending between the first and second end portions. The telescoping member is actuatable to decrease the distance between the first and second end portions and increase the distance between the bone segment and the source bone.

According to some implementations, the at least one telescoping member includes a first telescoping member having a first threaded portion threadably engageable with a second threaded portion. The first threaded portion can include a first rod having a series of external threads and a bore having a series of internal threads. The second threaded portion can include a second rod having a series of external threads. The external threads of the second rod can be threadably engageable with the internal threads of the first rod. In certain instances, one of the first and second end portions includes a bore having a series of internal threads such that the external threads of the second rod are threadably engageable with the internal threads of the bore of the one of the first and second end portions.

In some implementations, the at least one telescoping member includes a second telescoping member that includes a first non-threaded portion slidably engageable with a second non-threaded portion. In yet some implementations, the at least one telescoping member includes a third telescoping member that has a third non-threaded portion slidably engageable with a fourth non-threaded portion. In such implementations, the first telescoping member is positioned between the second and third telescoping members.

According to one implementation, the distractor is adjustable between a minimum overall length and a maximum overall length. The ratio of a maximum distance between the first and second end portions to the minimum overall length can be greater than about 14:9.

In another embodiment, a method for distracting a segment of bone from a source bone includes providing a bone distractor that has a first end portion and a second end portion movable relative to each other. The method further includes coupling the first end portion to the segment of bone and coupling the second end portion to an anchor bone opposing the source bone. Additionally, the method includes actuating the bone distractor to move the first and second end portions closer to each other and pull the segment of bone toward the anchor bone. The method can also include fixing the source bone relative to the anchor bone. Further, the method can include positioning the bone distractor to the sides of the source bone, anchor bone, and a gingival layer covering the bones.

In some implementations of the method, the bone distractor includes a threaded telescoping portion extending between the first and second end portions. In such implementations, actuating the bone distractor includes rotating the threaded telescoping portion relative to the first and second end portions. According to some implementations, at least one of the first and second end portions includes internal threads. The threaded telescoping portion can include a first member that has external threads and internal threads and a second member having external threads. In such implementations, rotating the threaded telescoping portion includes at least one of threadably engaging the internal threads of the first member with the external threads of the second member and threadably engaging the external threads of the first member with the internal threads of the at least one of the first and second end portions.

According to some implementations, coupling the first end portion to the segment of bone includes coupling the first end portion to at least one anchor embedded within the segment of bone and extending from a side of the segment of bone. Further, coupling the second end portion to the anchor bone can include coupling the second end portion to at least one anchor embedded within the anchor bone and extending from a side of anchor bone.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

Furthermore, the described features, advantages, and characteristics of the subject matter of the present disclosure may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments. These features and advantages will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

Furthermore, the details, including the features, structures, or characteristics, of the subject matter described herein may be combined in any suitable manner in one or more embodiments. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the disclosed subject matter.

Generally, described herein are embodiments of a bone distractor and associated apparatus, systems, and methods for lengthening a bone. In one embodiment, the distractor includes a threaded telescoping portion that is adjustable to pull a bone segment away from a source bone. The telescoping portion can include a first threaded rod insertable into and threadably engageable with a second threaded rod. The second threaded rod can be threadably engageable with an end portion or guide element. The threaded telescoping portion facilitates an increased action to length ratio compared to conventional distraction devices. Moreover, because the distractor pulls the bone segment, rather than pushes it, the control of the force vectors on the bone segment is increased compared to conventional distraction devices. Additionally, because the distractor pulls the bone segment, the distractor does not need to be secured or embedded within the patient's bone tissue as with conventional bone pulling distraction devices.

Figure 1:
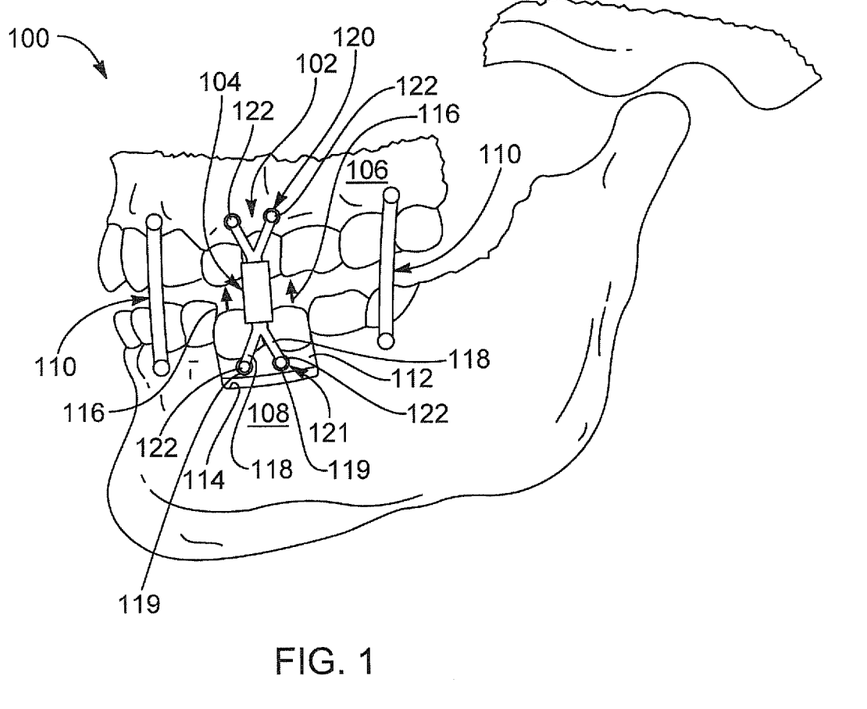
FIG. 1 is a side elevation view of a bone distraction system according to one representative embodiment.

One representative embodiment of a bone distraction system 100 is shown in FIG. 1. The bone distraction system 100 includes a distractor system 102 and at least one jaw fixator 110. In the illustrated embodiment, the bone distraction system 100 includes at least two jaw fixators 110. Each fixator 110 is secured to the jaw bones, i.e., the maxilla or upper jaw bone 106 and the mandible or lower jaw bone 108, at opposing ends. When secured to the jaw bones 106, 108, the fixators 110 hold the jaw in place to prevent the jaw from opening or otherwise preventing movement of the jaw bones 106, 108 relative to each other. The fixators 110 can be any of various maxilla-mandibular fixation devices commonly used in the art and any of various techniques known in the art can be used to secure the fixation devices to the jaw bones.

As will be described in more detail below, after the jaw bones 106, 108 are fixed relative to each other using the fixators 110, the bone distractor system 102 is secured to the jaw bones. The bone distractor system 102 includes a bone distractor 104 coupled to the jaw bones 106, 108 via a pair of connectors 120, 121. As shown, the connector 120 is secured to the maxilla jaw bone 106 by a pair of anchors 122 embedded in the maxilla jaw bone and the connector 121 is secured to a bone segment 112 of the mandible jaw bone 108 by a pair of anchors 122. Each anchor 122 is embedded into the respective bone or bone segment using any of various techniques known in the art, e.g., screwing the anchors 122 into the bone or bone segment. The connectors 120, 121 are fastened, or otherwise secured, to the bone distractor 104 and include a pair of arms 118 diverging away from the bone distractor 104. An eyelet 119 is positioned proximate an end of each arm 118. The eyelets 119 fit over a respective anchor 122 to secure the connectors 120, 121, and thus the bone distractor 104, to the jaw bone 106 and bone segment 112. Although the connectors 120, 121 illustrated in FIG. 1 have a generally "Y" shape with two eyelets 119, in other embodiments, the connectors can have any of various shapes and sizes and have any of a number of eyelets or anchor attachments.

The bone distractor 104 is configured to pull the bone segment 112 away from a source bone toward an anchor bone. The source bone is defined as the bone from which a bone segment is to be moved is cut and the anchor bone is defined as the bone toward which the bone segment is moved. In the illustrated embodiment, the source bone is the mandible jaw bone 108 and the anchor bone is the maxilla jaw bone 106. In other embodiments, however, the source bone can be the maxilla jaw bone 106 and the anchor bone can be the mandible jaw bone 108. Similarly, in non-oral applications, the source and anchor bones can be any other bones in the body in relative proximity to each other. As shown, the bone distractor 104 pulls the bone segment 112 away from the mandible jaw bone 108 and toward the maxilla jaw bone 106 in a direction indicated by arrows 116. The bone segment 112 is cut from the mandible jaw bone 108 along cut line 114. As the bone segment 112 moves away from the mandible jaw bone 108 at a predetermined rate or over predetermined increments, new bone tissue fills in the gap between the bone segment 112 and mandible jaw bone to effectively lengthen the mandible jaw bone.

Figure 2:
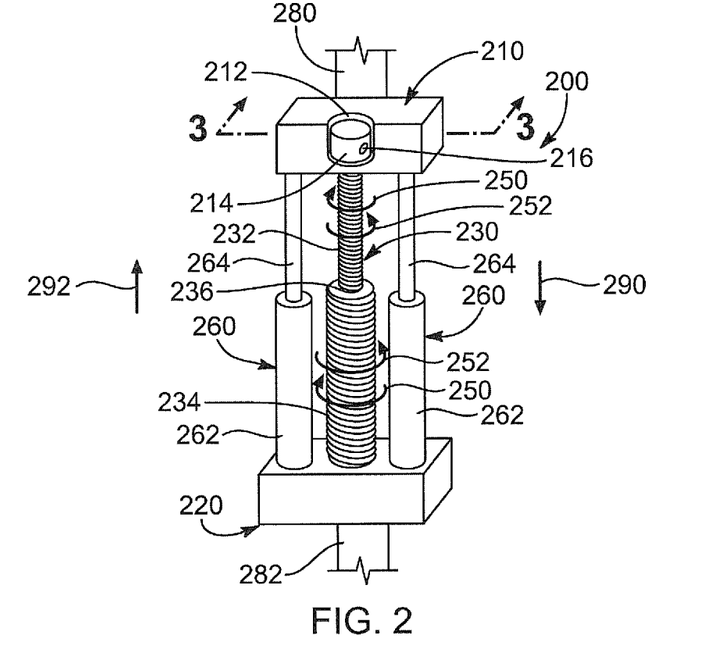
FIG. 2 is a perspective view of a bone distractor according to one representative embodiment shown in a fully open position.

Referring to FIG. 2, a bone distractor 200 is shown coupled to opposing connectors 280, 282. The bone distractor 200 can be used in place of bone distractor 104 and the connectors 280, 282 can be similar to connectors 120, 121. The bone distractor 200 includes first and second end portions 210, 220, respectively. As shown, the bone distractor 200 includes a threaded telescoping member 230 and two non-threaded telescoping members 260 extending between the first and second end portions 210, 220. Generally, the threaded telescoping member 230 is actuatable to adjust the overall distance $D_6$ between the first and second end portions 210, 220.

The first end portion 210, or top end portion as shown, includes a recess 212 sized and shaped to receive an adjustment knob 214. The recess 212 is formed in the first end portion 210 and configured to allow the adjustment knob 214 to be at least partially embedded within the first end portion. Desirably, the vertical heights of the first and second end portions 210, 212 are limited to reduce obstruction with portions of the client's mouth and/or other orthodontic appliances. Therefore, in certain implementations, the adjustment knob 214 is embedded within the first end portion 210 as shown such that the knob does not protrude from the top of the first end portion 210. Although less preferable, in some embodiments, the adjustment knob 212 can be secured to an outer surface of the first end portion 210 and protrude away from the first end portion. The adjustment knob 212 includes a tool engager 216, such as a specifically-shaped recess or aperture, for receiving an adjustment tool (not shown).

The adjustment knob 214 couples the threaded telescoping member 230 to the first end portion 210. More specifically, a first threaded rod 232 of the telescoping member 230 extends through an aperture 218 formed in the first end portion 210 that opens to the recess 212 (see FIG. 3). The first threaded rod 232 connects to the adjustment knob 214 such that rotation of the adjustment knob 214 correspondingly rotates the first threaded rod 232.

Figure 3:
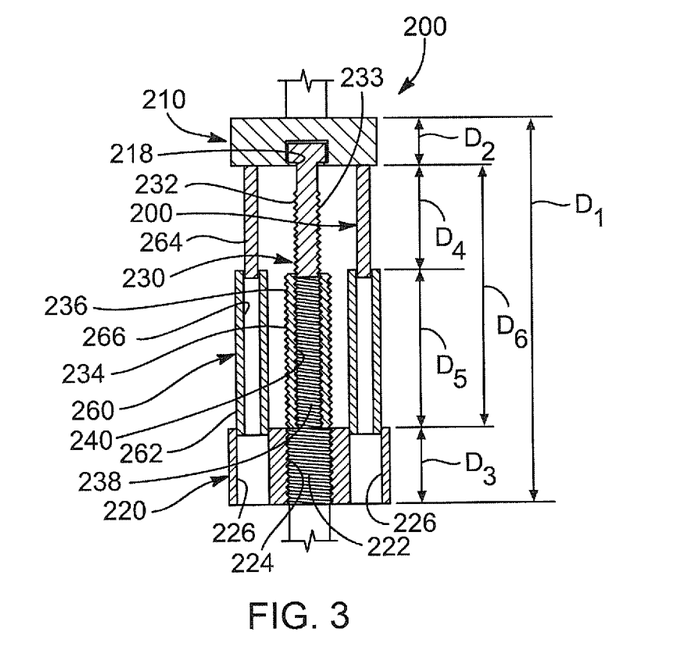
FIG. 3 is a cross-sectional side view of the bone distractor of FIG. 2 taken along the lines 3-3 of FIG. 2.

Referring to FIG. 3, the second end portion 220 includes a first aperture, e.g., first bore 222, extending through the second end portion. The first bore 222 is sized to receive a second threaded rod 234 of the threaded telescoping member 230. The diameter of the first bore 222 is just larger than the outer diameter of the second threaded rod 234. Moreover, a series of internal threads 224 are formed on an internal surface of the first bore 222. The pitch and diameter of the internal threads 224 correspond with the pitch and diameter of external threads 236 of the second threaded rod 234 such that the second threaded rod 234 is insertable into and threadably engageable with the first bore 222.

Referring again to FIG. 3, the second end portion 220 also includes a pair of second apertures, e.g., second bores 226, extending through the second end portion. Each second bore 226 is sized to receive a second rod 262 of a respective one of the non-threaded telescoping members 260. Generally, the outer diameters of the second rods 262 are approximately the same as the diameters of the second bores 226.

Although the illustrated first and second end portions 210, 220 are shown having a generally rectangular block shape, in other embodiments, the end portions can have any of various shapes and sizes conducive to the particular application for which the distractor 200 is being used.

The threaded telescoping member 230 includes the first threaded rod 232 in telescoping engagement with the second threaded rod 234. The first threaded rod 232 includes a series of external threads 233 extending along a substantial length of the first threaded rod. In certain implementations, the external threads 233 extend along the entire length of the first threaded rod 232. The second threaded rod 234 includes the external threads 236 as discussed above and internal threads 240 formed in an internal surface of a bore 238 extending through the second threaded rod 234. The thread pitch and diameter of the internal threads 240 of the second threaded rod 234 correspond to the thread pitch and diameter of the external threads 233 of the first threaded rod 232 such that the first threaded rod 232 is insertable into and threadably engageable with the bore 238 of the second threaded rod. The first threaded rod 232 and the second threaded rod 234 are telescopingly engageable because the first threaded rod can be inserted into the second threaded rod such that the second threaded rod overlaps the first threaded rod.

Moreover, while in telescoping engagement, as the first and second threaded rods 232, 234 are rotated relative to each other, the threaded engagement between the external and internal threads 233, 240, respectively, causes the threaded rods to move coaxially relative to each other in directions indicated by directional arrows 290, 292 (see FIG. 2). In other words, as the first threaded rod 232 is rotated relative to the second threaded rod 234, the first threaded rod 232 moves linearly along the bore 238 of the second threaded rod and the second threaded rod moves linearly along the outside of the first threaded rod. The overall effect of rotating the first threaded rod 232 and second threaded rod 234 relative to each other is an adjustment of the overall length of the bone distractor 200, the distance $D_4$ between the first end portion 210 and the second threaded rod, and the distance $D_6$ between the first and second end portions 210, 220 (see FIG. 3). More specifically, for threads 233, 240 with a left-handed thread pattern, rotation of the first threaded rod 232 in a clockwise direction 250 (see FIG. 2) relative to the second threaded rod 234 increases the distances $D_4$ and $D_6$. Similarly, rotation of the first threaded rod 232 in a counterclockwise direction 252 relative to the second threaded rod 234 decreases the distances $D_4$ and $D_6$.

Concurrently with or separately from the first threaded rod 232 rotating relative to the second threaded rod 234, the second threaded rod 234 is rotatable relative to the second end portion 220. More specifically, the external threads 236 of the second threaded rod 220 are threadably engageable with the internal threads 224 of the first bore 222 such that rotation of the second threaded rod 232 causes the second threaded rod to move linearly along the first bore 222 in one of directions 290, 292 depending on the direction of rotation. The overall effect of rotating the second threaded rod 234 is an adjustment of the overall length of the bone distractor 200, the distance $D_5$ between the first threaded rod 232 and the second end portion 220, and the distance $D_6$ between the first and second end portions 210, 220 (see FIG. 3). More specifically, for threads 224, 236 with a left-handed thread pattern, rotation of the second threaded rod 234 in a clockwise direction 250 (see FIG. 2) relative to the second end portion 220 increases the distances $D_5$ and $D_6$. Similarly, rotation of the second threaded rod 234 in a counterclockwise direction 252 relative to the second end portion 220 decreases the distances $D_5$ and $D_6$. Although the illustrated threads have a left-handed thread pattern, in other embodiments, the threads can have a right-handed thread pattern such that rotating the threaded rods in the clockwise direction 250 decreases the distances $D_4$, $D_5$, $D_6$, and rotating the threaded rods in the counterclockwise direction 252 increases the distances $D_4$, $D_5$, $D_6$.

Figure 4:
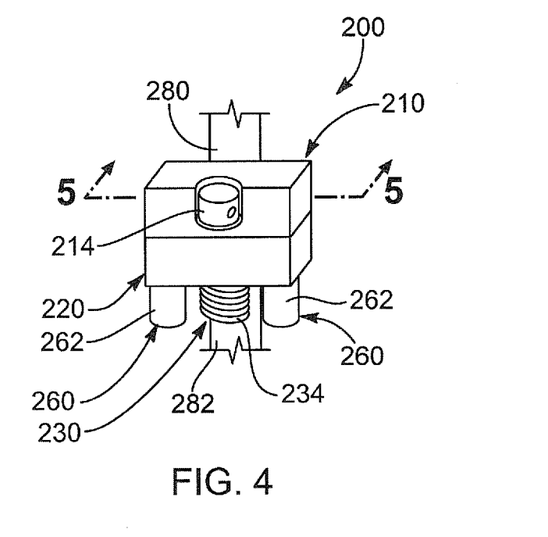
FIG. 4 is a perspective view of the bone distractor of FIG. 2 shown in a fully closed position.
Figure 5:
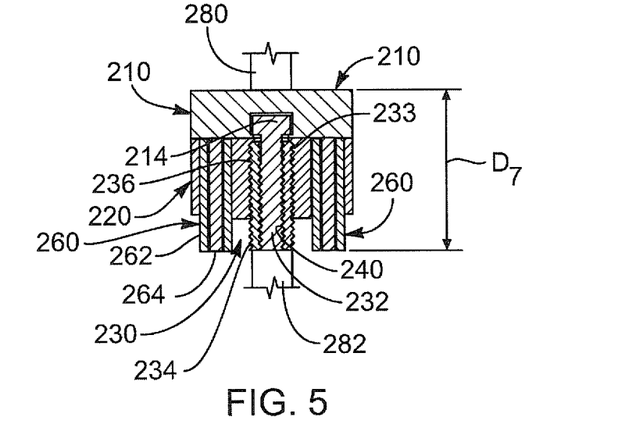
FIG. 5 is a cross-sectional side view of the bone distractor of FIG. 4 taken along the lines 5-5 of FIG. 4.

The bone distractor 200 is adjustable between a maximum overall length $D_1$ (see FIG. 3) and a minimum overall length $D_7$ (see FIG. 5). As shown in FIGS. 2 and 3, when the distractor 200 is at the maximum overall length $D_1$, the distractor is in a fully open position. Similarly, as shown in FIGS. 4 and 5, when the distractor 200 is at the minimum overall length $D_7$, the distractor is in a fully closed position. Further, the distractor 200 is adjustable to any of various positions intermediate the fully open and closed positions.

In certain implementations, the overall length of the distractor is at the maximum overall length $D_1$, i.e., in the fully open position, when the distance $D_4$ is approximately equal to the total length of the first threaded rod 232 and the distance $D_5$ is approximately equal to the total length of the second threaded rod 234. Accordingly, the first threaded rod 232 can be rotated in the clockwise direction 250 until the distance $D_4$ is approximately equal to the total length of the first threaded rod and the second threaded rod 234 can be rotated in the clockwise direction until the distance $D_5$ is approximately equal to the total length of the second threaded rod.

The minimum overall length $D_1$ of the distractor 200 is the overall length of the distractor when the distances $D_4$, $D_5$ are each equal to approximately zero, e.g., when the first and second end portions 210, 220 are in contact with each other. The distractor 200 can be adjusted to the minimum overall length $D_7$, i.e., into the fully closed position, by rotating the first and second threaded rods 232, 234 in the counterclockwise direction 252 until the distances $D_4$, $D_5$ are each equal to approximately zero. As shown in FIG. 5, in certain embodiments, when the distractor 200 is in the fully closed position, the first and second threaded rods 232, 234 (with the first threaded rod being within the bore 238 of the second threaded rod) extend from the second end portion 220 in a direction away from the first end portion 210.

The maximum distance $D_6$, e.g., the maximum distance $D_4$ plus the maximum distance $D_5$, corresponds with a maximum action capability or maximum range of motion of the bone distractor 200. As defined herein, the maximum range of motion is the maximum distance a distractor can move a bone segment in a bone distraction process. Typically, bone distractors are rated according to an action to length ratio, i.e., a ratio of the maximum range of motion of the distractor to the minimum overall length of the distractor. For some conventional bone distractors, a typical action to length ratio is no more than about 11:15. Generally, because of the threaded telescoping member 230, e.g., the threaded rod within a threaded rod configuration, the action to length ratio of the bone distractor of the present application is higher than conventional distractors. According to various embodiments of the bone distractor of the present application, e.g., bone distractor 200, the action to length ratio is between about 11:15 and about 14:9. In one particular embodiment, the action to length ratio of the bone distractor 200 is about 14:9. The higher action to length ratios of the distractors described herein allow for smaller and more compact distractors, while providing greater ranges of motion, than conventional distractors. These characteristics facilitate easier placement and flexibility in the distraction osteogenesis process, as well as to reduce the discomfort often associated with large and cumbersome bone distraction devices.

Referring back to FIG. 2, the bone distractor 200 includes the non-threaded telescoping members 260 for providing structural support and rigidity to the distractor. Each non-threaded telescoping member 260 includes a first rod 264 in telescoping engagement with the second rod 262. The first rod 264 is secured to the first end portion 210 and extends at least partially within a bore 266 formed in the second rod 262. Likewise, the second rod 262 extends at least partially within a respective one of the second bores 226 formed in the second end portion 220. Although the distractor 200 includes two non-threaded telescoping members 260 in the illustrated embodiment, in other embodiments, the distractor can have one or more than two non-threaded telescoping members as desired.

The non-threaded telescoping members 260 actuate concurrently with actuation of the threaded telescoping member 230. In other words, as the first and second threaded rods 232, 234 are rotated to increase or decrease the distance $D_6$ between the first and second end portions 210, 220, the first rod 264 correspondingly moves along the bore 266 and/or the second rod 262 correspondingly moves along a respective second bore 226. For example, when the distractor 200 is moved into the fully closed position (see FIG. 5), the first rod 264 moves in the direction 290 relative to the second rod 262 until the entire first rod is within the second rod. As shown in FIG. 5, in certain instances, when the distractor 200 is in the fully closed position, the first and second rods 264, 262 of the respective non-threaded telescoping members 260 protrude from the second end portion 220 away from the first end portion 210.

In some embodiments, the distractor 200 includes a stop for preventing disengagement between the first threaded rod 232 and second threaded rod 234. In other words, the stop prevents the distractor 200 from actuating beyond the fully open position. In one embodiment, the stop includes one or more pins engageable with corresponding grooves that extend along the inner surface of the bore 266. The grooves can terminate just prior to the opening of the bore 266. As the distractor 200 is opened, the pins slide along the grooves until they contact an end of the grooves, which prevents further movement of the pins and movement of the first end portion 210 away from the second end portion 220. In other embodiments, the stop can be any of various stop mechanisms known in the art.

Figure 6:
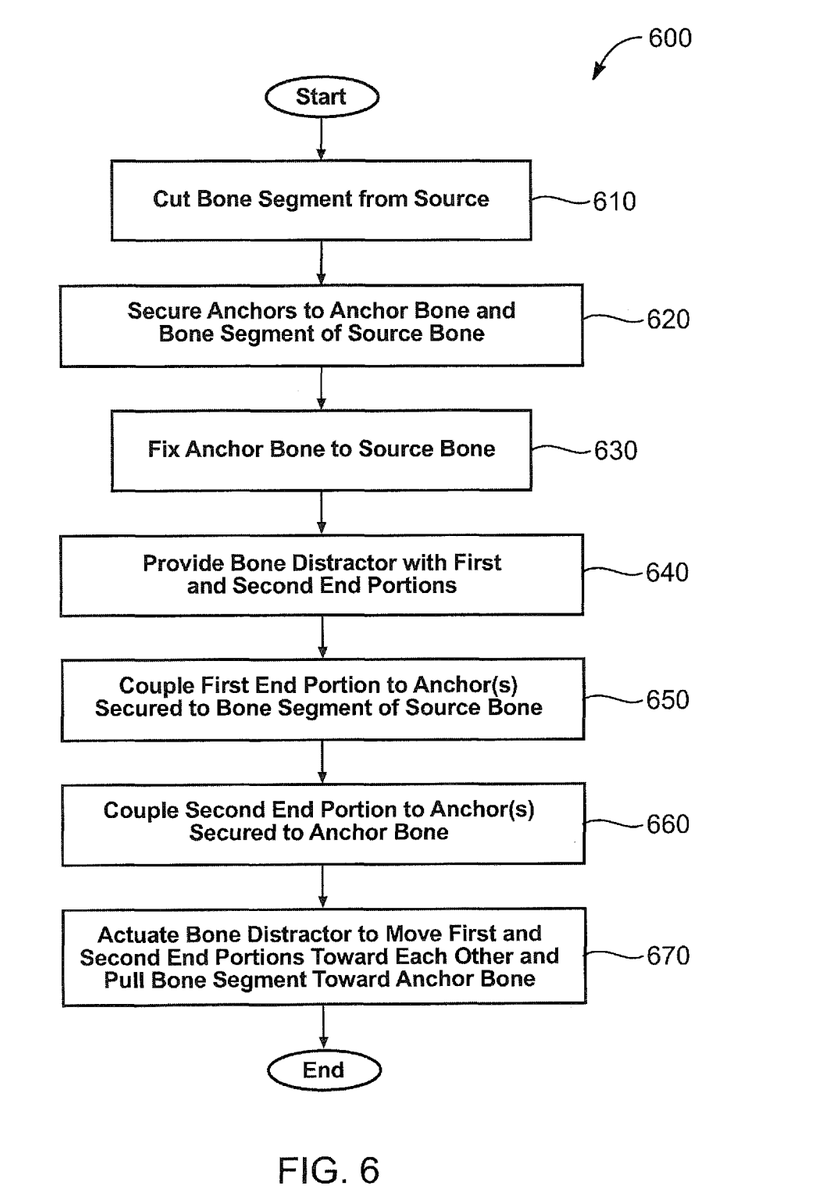
FIG. 6 is a schematic diagram of a method for distracting a bone segment using a bone distractor.

Referring to FIG. 6, a method 600 is shown for distracting a bone segment using a bone distractor, e.g., distractor 200, according to one representative embodiment. The method includes cutting 610 a bone segment from a source bone, e.g. the mandible jaw bone 108. The bone segment represents a width of bone to be lengthened. Cutting 610 the bone segment can include any of various methods known in the art. For example, in the illustrated embodiment, cutting 610 the bone segment 112 includes cutting the mandible jaw bone 108 along the cut line 114. The bone segment 112 can be cut with minimal degloving of the overlying soft tissue and minimal disruption of the blood supply. Any open overlying soft tissue is closed after cutting 610 the bone segment 112. After cutting 610 the bone segment 112, in one implementation, the bone segment 112 is stabilized in its original location relative to the source bone for a desired period of time, e.g., one week, to allow growth of elastic fibers between the source bone and bone segment.

Before, or after, cutting 610 the bone segment, anchors, e.g., anchors 122, are secured 620 to the bone segment and the anchor bone, e.g., maxilla jaw bone 106. For example, in the illustrated embodiment, two anchors 122 are secured to the bone segment 112 and two anchors 122 are secured to the maxilla jaw bone 106. In certain implementations, the anchors 122 are screw-like elements and securing 620 the anchors includes screwing the anchors into the bone. In some situations, a pilot hole can be drilled into to bone to facilitate proper embedment and orientation of the anchor 122 in the bone. In one implementation, after securing 620 the anchors in place, the method 600 includes fixing, e.g., wiring, 630 the anchor bone to the source bone using any of various fixation techniques and devices known in the art. In one implementation, jaw fixators 110 are used to wire 630 the anchor bone to the source bone. Wiring the anchor bone to the source bone can provide vertical stability of the jaw bones.

The method 600 further includes providing 640 a bone distractor with first and second end portions. In certain embodiments, the bone distractor can be the bone distractor 200 shown in FIGS. 2-4 and the first and second end portions can be first and second end portions 210, 220. The first end portion is coupled 650 to the anchors 122 secured to the bone segment. Similarly, the second end portion is coupled 660 to the anchors 122 secured to the anchor bone. Coupling 650, 660 of the first and second end portions to the anchors 122 can be facilitated by a pair of connectors each coupled to a respective end portions and each having anchor engaging portions, e.g., eyelets 119. The first and second end portions are coupled 660 to the anchors by positioning the eyelets 119 of the connectors over or about the head portions.

Figure 7A:
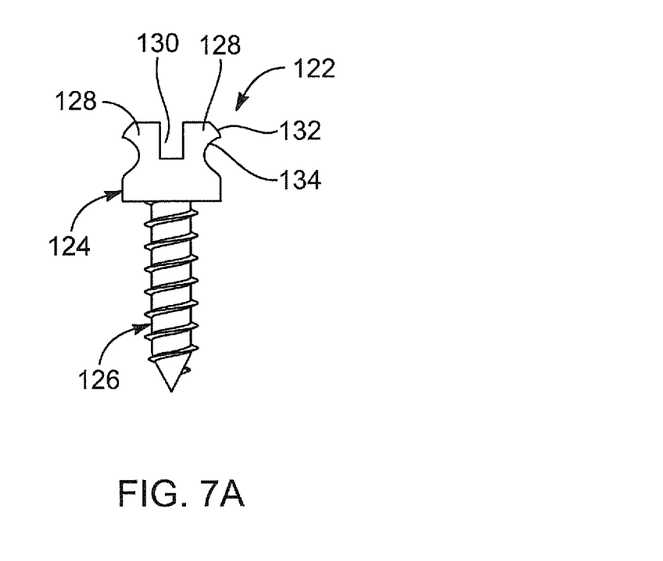
FIG. 7A is a side elevation view of an anchor of a bone distraction system according to one embodiment.
Figure 7B:
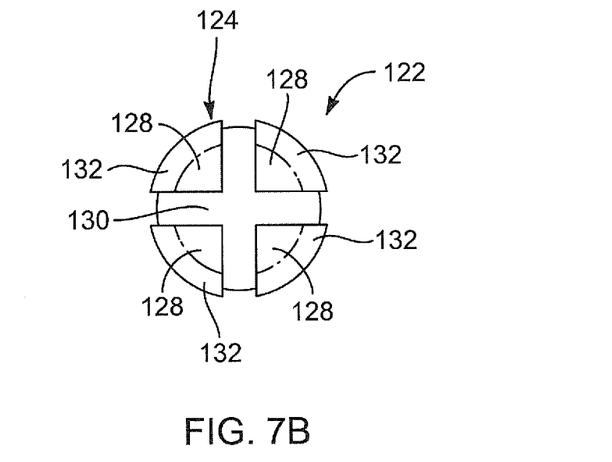
FIG. 7B is a top plan view of the anchor of FIG. 7A.

As shown in FIGS. 7A and 7B, in some implementations, the anchors 122 each include a head portion 124 and a threaded portion 126. The threaded portion 126 is embedded, e.g., screwed, into the patient's gingival and bone tissue such that the head portion 124 is exposed on the outer surface of the patient's tissue. The head portion 124 includes a plurality of resiliently movable tabs 128 to facilitate removable attachment of the eyelets 119 to the anchors. The tabs 128 each have a beveled portion 132 to facilitate ease in coupling the eyelets 119 to the anchors 122 and a concave portion 134 opposing the beveled portion 132 to assist in retaining the eyelets 119 on the head portion 124. Generally, the concave portions 134 make it harder to remove the eyelets 119 than to attach the eyelets. In an unflexed state, the outer surfaces of the tabs 128 define a circumference having a diameter slightly larger than an inner diameter of the eyelets 119.

The tabs 128 are configured to flex inwardly toward each other as an eyelet 119 is positioned about and slid onto the head portion 124 toward the threaded portion 126. As the eyelet 119 slides past the tabs, 128, the tabs rebound back to their original shape thus retaining the eyelet on the section of the head portion 124 intermediate the tabs and the threaded portion 126. The eyelet 119 is removed from the head portion 124 by pulling or sliding the eyelet away from the threaded portion 126 and against the tabs 128 with sufficient force to overcome the bias of the tabs and flex the tabs inwardly such that the eyelet can be slid off of the head portion 124. The anchor 122 includes a tool engagement portion 130 defined between the tabs 128. A fastening tool, such as a flathead or Phillips screw driver, can engage the tool engagement portion 130 to secure the anchor 122 to the patient's jaw.

Preferably, as shown in the illustrated embodiments, the bone distractor is intra-oral. In other words, the bone distractor shown is not embedded within, inserted into, or otherwise positioned within the bone, gingival, or other tissue of the jaw. For example, the distractor 200 is a para-jaw distractor positioned to the side of the jaw, as opposed to being embedded within the jaw. Because the bone distractor 200 is to the side of the jaw, the adjustment knob 214 is easily accessible to provide for easy adjustment of the distractor. Further, because the bone distractor 200 is not embedded within the jaw tissue, the risk of infection is reduced compared to bone distractors that are embedded within the jaw tissue, such as via invasive surgical procedures.

After the first and second end portions are secured 650, 660 to the anchors 122, the bone distractor is actuated 670 to move the first and second end portions toward each other and pull the bone segment toward the anchor bone. Referring to distractor 200, actuating 670 the distractor 200 includes pulling the bone segment 112 towards the maxilla jaw bone 106 by rotating the adjustment knob 214 in a counterclockwise direction. The adjustment knob 214 can be rotated by inserting an adjustment tool, such as a wire or hexagonal wrench, into the tool engager 216 and applying a rotational force to the adjustment tool.

In certain embodiments, actuating 670 the distractor includes incrementing the rotation of the adjustment tool according to a predefined actuation schedule. For example, after initial coupling of the distractor 200 to the bone segment 112 and maxilla jaw bone 106, the doctor can actuate 670 the distractor into a starting position. For example, when initially coupled to the bone segment 112 and maxilla jaw bone 106, the distractor 200 can be in the fully open position. The doctor then actuates 670 the distractor 200 to place the distractor in some position intermediate the fully open and fully closed positions. The starting position can correspond to a predetermined initial gap between the bone segment 112 and the mandible jaw bone 108. After setting the distractor 200 in the starting position, the doctor, the patient, or a third party intermittently rotates the adjustment knob according to the actuation schedule to move the bone segment incrementally closer to the anchor bone.

Based on the thread pattern of the threads 224, 233, 236, 240, each full rotation of the adjustment knob corresponds to a predetermined range of motion or action or the first and second end portions 210, 220, e.g., a predetermined decrease in the distance $D_6$. Accordingly, from the starting position, the predefined actuation schedule may require periodically rotating the adjustment tool a predetermined amount to pull the bone segment 112 toward the anchor bone 106 a predetermined distance. In specific implementations, each full rotation of the adjustment knob 214 corresponds to one millimeter of action or a reduction of one millimeter from the distance $D_6$. Therefore, in some instances, depending on the patient's particular characteristics, the predefined actuation schedule may request a quarter turn of the adjustment knob 214 every day to move the bone segment 112 a quarter of a millimeter each day. Of course the amount of rotation or action of the bone segment 112 and the frequency of the rotations can vary from patient to patient and from condition to condition.

The intermittent adjustment of the distractor 200 continues until a desired result in achieved, at which time the distractor and anchors in the anchor bone can be removed from the patient. With the distractor removed, the bone segment can be stabilized in its new location relative to the source bone using the anchors in the bone segment to allow the bone segment to heal in the new location. Once healed, the anchors can be removed from the bone segment.

The schematic flow chart diagrams herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for distracting a segment of bone from a source bone, the method comprising:
   providing a bone distractor comprising a first end portion and a second end portion movable relative to each other;
   coupling the first end portion directly to the segment of bone;
   coupling the second end portion directly to an anchor bone opposing the source bone, the anchor bone being a naturally different bone than the source bone; and
   actuating the bone distractor to move the first and second end portions closer to each other and pull the segment of bone toward the anchor bone.

2. The method of claim 1, further comprising fixing the source bone relative to the anchor bone.

3. The method of claim 1, wherein the bone distractor comprises a threaded telescoping portion extending between the first and second end portions, and wherein actuating the bone distractor comprises rotating the threaded telescoping portion relative to the first and second end portions.

4. The method of claim 3, wherein:
   at least one of the first and second end portions comprises internal threads;
   the threaded telescoping portion comprises a first member having external threads and internal threads and a second member having external threads; and
   rotating the threaded telescoping portion comprises at least one of threadably engaging the internal threads of the first member with the external threads of the second member and threadably engaging the external threads of the first member with the internal threads of the at least one of the first and second end portions.

5. The method of claim 1, wherein:
   coupling the first end portion to the segment of bone comprises coupling the first end portion to at least one anchor embedded within the segment of bone and extending from a side of the segment of bone; and
   coupling the second end portion to the anchor bone comprises coupling the second end portion to at least one anchor embedded within the anchor bone and extending from a side of anchor bone.

6. The method of claim 1, further comprising positioning the bone distractor to the sides of the source bone, anchor bone, and a gingival layer covering the bones.

7. A method for distracting a bone segment of a source bone from the source bone, the method comprising:
    immovably fixing the source bone relative to an anchor bone;
    movably fixing the bone segment of the source bone directly to the anchor bone; and
    with the source bone immovably fixed relative to the anchor bone and the bone segment movably fixed to the anchor bone, pulling the bone segment of the source bone toward the anchor bone;
    wherein the anchor bone comprises one of the maxilla jaw bone and mandible jaw bone and the source bone comprises the other of the maxilla jaw bone and mandible jaw bone.

8. The method of claim 7, wherein pulling the bone segment of the source bone toward the anchor bone comprises decreasing a distance between the anchor bone and the bone segment of the source bone.

9. The method of claim 7, further comprising cutting the bone segment away from the source bone.

10. The method of claim 9, wherein cutting the bone segment comprises cutting the bone segment along a cut line, and wherein pulling the bone segment of the source bone toward the anchor bone comprises increasing a distance between the bone segment of the source bone and the cut line.

11. The method of claim 7, wherein the bone segment of the source bone is separated from the source bone along a cut line, and wherein pulling the bone segment of the source bone toward the anchor bone comprises increasing a distance between the bone segment of the source bone and the cut line.

12. A method for distracting a segment of bone from a source bone, the method comprising:
    providing a bone distractor comprising a first end portion and a second end portion movable relative to each other;
    coupling the first end portion to the segment of bone;
    coupling the second end portion to an anchor bone opposing the source bone; and
    actuating the bone distractor to move the first and second end portions closer to each other and pull the segment of bone toward the anchor bone;
    wherein the bone distractor comprises a threaded telescoping portion extending between the first and second end portions, and wherein actuating the bone distractor comprises rotating the threaded telescoping portion relative to the first and second end portions; and
    wherein at least one of the first and second end portions comprises internal threads, the threaded telescoping portion comprises a first member having external threads and internal threads and a second member having external threads, and rotating the threaded telescoping portion comprises at least one of threadably engaging the internal threads of the first member with the external threads of the second member and threadably engaging the external threads of the first member with the internal threads of the at least one of the first and second end portions.

* * * * *